United States Patent
Gwon et al.

[11] Patent Number: 5,300,114
[45] Date of Patent: Apr. 5, 1994

[54] SUBCONJUNCTIVAL IMPLANTS FOR OCULAR DRUG DELIVERY

[75] Inventors: Arlene E. Gwon, Newport Beach; David Meadows, Mission Viejo, both of Calif.

[73] Assignee: Allergan, Inc., Irvine, Calif.

[21] Appl. No.: 926,402

[22] Filed: Aug. 10, 1992

Related U.S. Application Data

[62] Division of Ser. No. 878,034, May 4, 1992, Pat. No. 5,178,635.

[51] Int. Cl.$^5$ .............................................. A61F 2/14
[52] U.S. Cl. ........................................... 623/4; 623/5
[58] Field of Search ................................. 623/5, 6, 4; 604/294–302, 890.1, 891.1, 892.1; 424/7.1, 9, 422, 423, 424; 514/912; 356/317, 318, 417

[56] References Cited

U.S. PATENT DOCUMENTS

| | | | |
|---|---|---|---|
| 3,916,899 | 11/1975 | Theeuwes et al. | 604/294 |
| 3,961,628 | 6/1976 | Arnold | 604/294 |
| 3,995,635 | 12/1976 | Higuchi et al. | 604/294 |
| 4,186,184 | 1/1980 | Zaffaroni | 424/14 |
| 4,863,457 | 9/1989 | Lee | 604/294 |
| 5,030,230 | 7/1991 | White | 623/5 |
| 5,098,443 | 3/1992 | Parel et al. | 604/294 |

*Primary Examiner*—Randall L. Green
*Assistant Examiner*—Debra S. Brittingham
*Attorney, Agent, or Firm*—Walter A. Hackler

[57] ABSTRACT

A system for providing controlled release of an active agent in an eye includes a device with a shape thereof for enabling placement of the device under a conjunctiva of an eye and additionally preventing migration of the device in the eye after placement of the device under the conjunctiva. The device may be formed of a material permeable to the passage of an agent disposed in said device. In addition, a tracer may be incorporated in the device to enable visual indication of the amount of active agent in said device when said device is disposed under the conjunctiva. To selectively treat specific areas of the eye, an impermeable layer may be provided for preventing diffusion of the active agent from a selected area of the device.

15 Claims, 3 Drawing Sheets

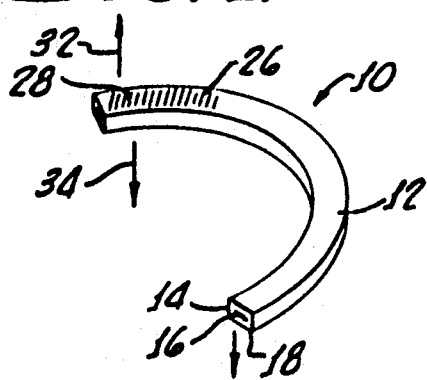
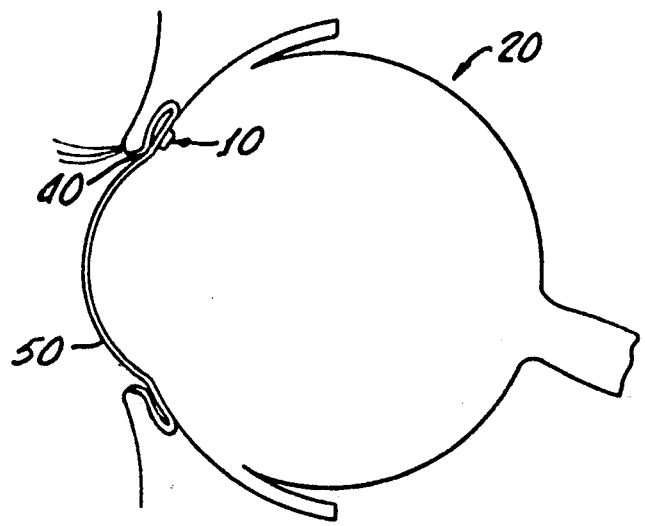
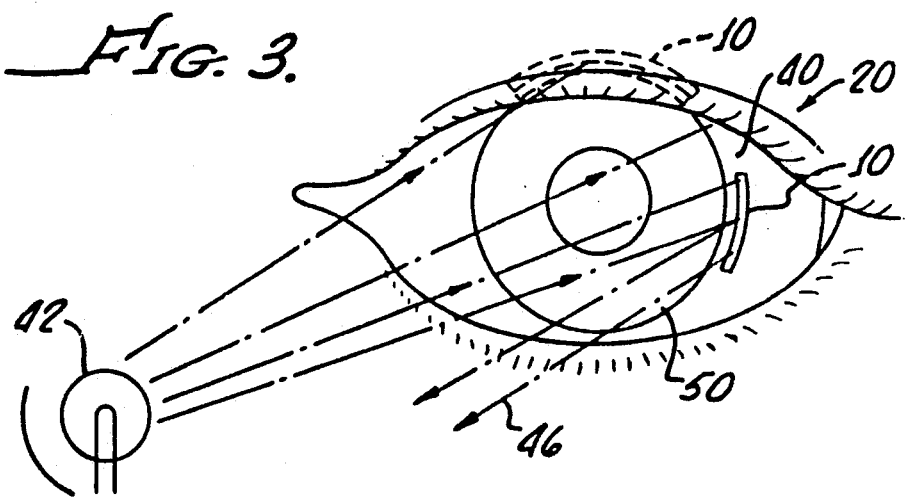
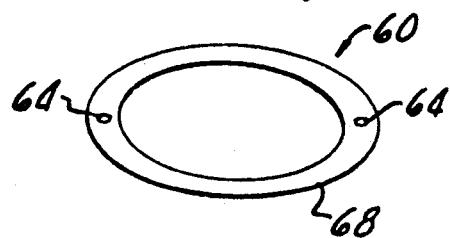
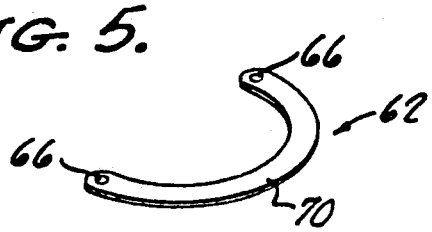

SUBCONJUNCTIVAL IMPLANTS FOR OCULAR DRUG DELIVERY

This application is a division of application Ser. No. 07/878,034, filed May 4, 1992, now U.S. Pat. No. 5,178,635.

The present invention is generally related to a system for providing controlled release of an active agent in an eye and particularly directed to a subconjunctival ocular implant for controlled release of an active agent.

Historically, treatment of eye conditions has usually been effected through the use of applied ophthalmic drugs in either liquid or ointment form.

However, in many instances, it is preferable to release a pharmaceutical agent acceptable at a controlled and/or continuous rate over a prolonged period of time in order to obtain a desired pharmacological effect. It is well known that such continuous delivery of a drug, or an active agent, is not obtainable through the use of liquid or ointment application, despite periodic application of these medications. Even with the controlled dispensing of liquid eye drops, for example, the level of medication in the eye varies dramatically because of the washing effect of tears which can substantially decrease the amount of available medication until the next application of those drops.

With specific reference to particular eye conditions, glaucoma is reportedly controlled by the release of pilocarpine which is dispensed from a thin film drug-delivery device inserted beneath an eyelid. Such ocular inserts are typically fabricated from flexible polymeric material which retains its integrity and therefore remains intact during the course of therapy. Ocular inserts containing pilocarpine are disclosed in U.S. Pat. Nos. 4,052,505 and 4,057,619.

Unfortunately, such ocular inserts generally require patient self-administration and in many instances may cause eye irritation. Concomitant problems associated with the use of ocular inserts include the necessity for patient education on insertion and removal which require a sufficient degree of manual dexterity on the part of the patient. This may be particularly important for the geriatric population. In addition, inadvertent loss of the ocular device due to lid laxity is a persistent problem with such devices.

In connection with the development of such devices, a number of excellent diffusion barriers for the control and release of drugs has been found, such as the ethylene-vinyl acetate polymers set forth in U.S. Pat. No. 1,052,505. This patent is directed to devices formed from flexible bodies of ethylene-vinyl acetate polymer containing ophthalmic drug compositions such as pilocarpine, which is dispensed to the eye by diffusion through the copolymer. While general reference is made to use of such barriers in implants for releasing a drug in the tissues of a living organism, the device disclosed is particularly adapted for insertion in the cul-de-sac of the conjunctiva between the bulbar conjunctiva and lid to be held in place against the eyeball by the pressure of the lid.

The subconjunctival ocular implant, in accordance with the present invention, overcomes the salient disadvantages of the hereinabove described ocular therapeutic systems which must be inserted into and removed from the cul-de-sac of the conjunctiva.

SUMMARY OF THE INVENTION

A system for providing controlled release of an active agent in an eye, in accordance with the present invention, generally includes a device having means defining a shape thereof for enabling placement of the device under a conjunctiva of an eye and more importantly, the shape is specifically designed for preventing migration of the device in the eye after placement of the device under the conjunctiva. Alternatively, means may be provided for enabling suturing of the device to the sclera of an eye. Yet another means for preventing migration of the device includes use of an adhesive for temporarily bonding the device to the conjunctiva.

The device is formed from a material permeable to the passage of active agent, and an active agent is provided and disposed in the device. The device would be implanted by a physician via routine outpatient procedure. Hence, the system of the present invention eliminates the need for patient self-administration, and therefore the patient's lifestyle is not encumbered by any need to remember to take medication by way of eye drops, or to have the manual dexterity necessary to insert and remove the device.

Additionally, an important feature of the present invention includes means for providing visual indication of the amount of active agent in the device when the device is disposed under the conjunctiva. This enables any physician to determine, over a period of time, in a quantitative manner, the amount of medication released over a period of time and the amount of active agent remaining in the device for future therapeutic treatment of the eye.

Thus, it is intended that following surgical implant of the device by a physician, periodic follow-up visits will enable the physician to visually determine and document the status of the eye treatment without removal of the device from the patient's eye. However, such devices can of course be removed on a periodic basis as well, thus obviating the need for the visual indicator system.

Specifically, the means for providing visual indication of the active agent in the device may comprise a fluorescent tracer and accordingly, a method in accordance with the present invention for indicating the amount of medication in the device includes the disposing of the device between a tissue layer of the subject and visually observing the indicated amount of medication in the device through the tissue layer. When a fluorescent tracer is utilized, the present method further includes the illumination of the device through the conjunctiva layer in order to visually observe the indicated amount of medication.

More particularly, a subconjunctival ocular implant, in accordance with the present invention, further includes means for supporting the active agent and enabling diffusion of the active agent out of the implant at a selected rate. In addition, means may be provided for preventing diffusion of the active agent from a selected area of the device in order to direct the diffusion of the active agent into selective areas of the eye, for example, posterior segments of the eye, such as the lens, the vitreous cavity and choroid/retina which are typically not treated effectively by either topical eye drops or eyelid-type inserts.

BRIEF DESCRIPTION OF THE DRAWINGS

The advantages and features of the present invention will be better understood by the following description when considered in conjunction with the accompanying drawings in which:

FIG. 1 is a perspective view of the subconjunctival ocular implant in accordance with the present invention;

FIG. 2 is a cross-sectional representation of the device implanted underneath the conjunctiva of an eye above the cornea thereof;

FIG. 3 is a front view representation of an eye having two devices in accordance with the present invention implanted beneath the conjunctiva;

FIGS. 4 and 5 are perspective view of alternative embodiments of the present invention showing openings in the devices for enabling suturing of the devices to the sclera of an eye;

DETAILED DESCRIPTION OF THE DRAWINGS

Figure 6:
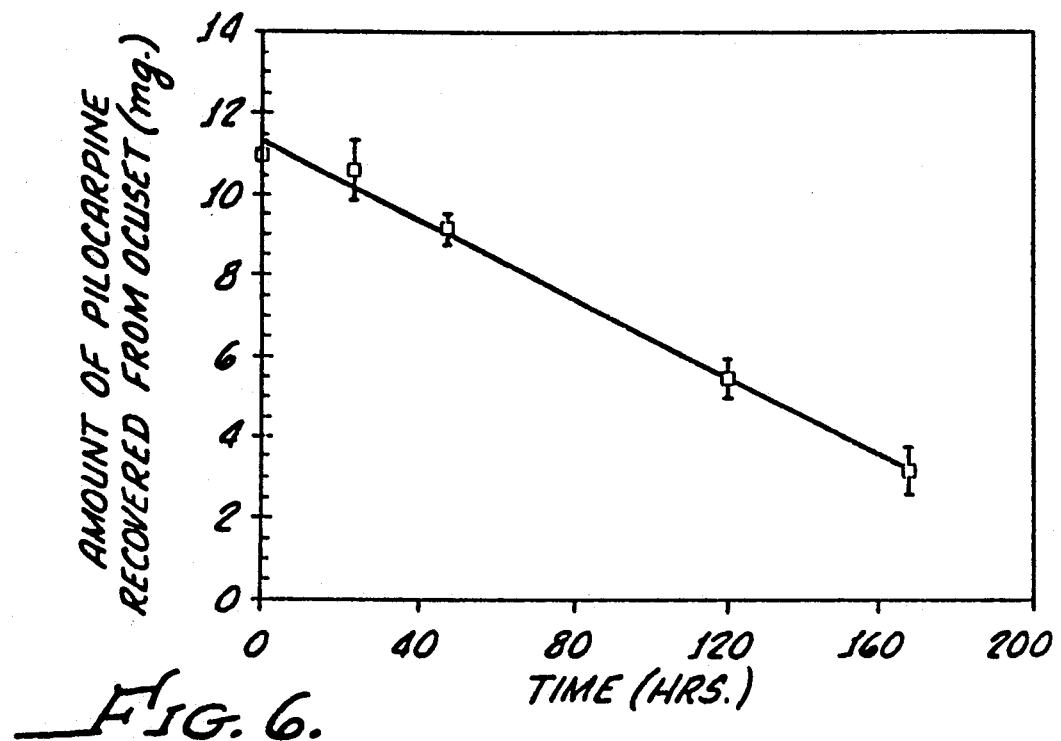
FIG. 6 is a plot of the amount of pilocarpine remaining in a device as a function of time.

Turning now to FIG. 1, there is shown subconjunctival ocular implant 10 in accordance with the present invention which generally includes a flexible body 12 formed of polymeric material. Materials suitable for use in the present invention may include those described in U.S. Pat. Nos. 4,052,505 and 4,057,619. Specifically, ethylene-vinyl acetate copolymers may be used as diffusion control materials. Ethylene-vinyl acetate copolymer acts as a rate controlling barrier which permits passage of an active agent, or drug, through the polymer by diffusion at a relatively low rate. Normally, the rate of passage of the active agent through the polymer is dependent on the solubility of the drug therein, as well as on the thickness of the polymeric barrier.

Other suitable materials for diffusion barriers include polymethyl methacrylate, polybutylmethacrylate, plasticized or unplasticized polyvinyl chloride, plasticized nylon, plasticized soft nylon, plasticized polyethylene terephthalate, natural rubber, polyisoprene, polyisobutylene, polybutadiene, polyethylene, silicone rubbers, polydimethylsiloxanes, and silicone-carbonate copolymers.

As is well known, the body 12 may include a solid inner matrix 14 having particles 16 of active agent dispersed therethrough. Various solid materials may be used to form the solid matrix having particles 16 of active agent. Essentially, any solid material chemically compatible with the active agent and permeable to passage of the active agent by diffusion can be used.

An outer polymeric membrane may be provided which surrounds the matrix 14 and provides an insoluble barrier to body fluids. Both the matrix material 14 and the membrane 18 are permeable to the passage of the active agent by diffusion with the materials selected, as is well known, to control the release of the active agent with the materials selected, which may be, for example, pilocarpine.

The arcuate shape of the device provides a means for preventing migration of the device in the eye 20 and at various positions as shown n FIGS. 2 and 3.

Other suitable drugs can be used in therapy of the eye with the ocular implant in accordance with the present invention include, by way of example only, but are not limited to:

Anti-infectives: such as antibiotics, including tetracycline, chlortetracycline, bacitracin, neomycin, polymyxin, gramicidin, oxytetracycline, chloramphenicol, and erythromycin; sulfonamides, including sulfacetamide, sulfamethizole, sulfisoxazole; quinolones, including ofloxacin, norfloxacin, ciprofloxacin, sporfloxacin; aminoglycosides including amikacin, tobramycin, gentamicin; cephalosporins; antivirals, including idoxuridine, trifluridine, vidarabine and acyclovir; antifungals such as amphotericin B, nystatin, flucytosine, natamycin, miconazolo and ketoconazole; and other anti-infectives including nitrofurazone and sodium propionate.

Antiallergenics: such as antazoline, methapyriline, chlorpheniramine, pyrilamine and prophonpyridamino; mast cell stabilizors such as cromolyn sodium.

Anti-inflammatories: such as hydrocortisone, hydrocortisone acetate, dexamethasone, dexamethasone 21-phosphate, fluocinolone, medrysone, prednisolone, prednisolone 21-phosphate and prednisolone acetate.

Nonsteroidal anti-inflammatories: such as flurbiprofen, suprofen, diclofenac, indomethacin, ketoprofen.

Decongestants: such as phenylephrine, naphazoline, and tetrahydrazoline.

Miotics and anticholinesterases: such as pilocarpine, eserine talicylate, carbachol, diisopropyl fluorophosphate, phospholine iodide, and demecarium bromide.

Mydriatics: such as atropine sulfate, cyclopentolate, homatropine, scopolamine, tropicamide, eucatropine, and hydroxyamphetamine.

Also useful in the present invention are:

Antiglaucoma agents: such as adrenergics—including epinephrine and dipivefrin; b-adrenergic blocking agents—including levobunolol, betaxolol, metipranolol, timolol; a-adrenergic agonists—including apraclonidine, clonidine; parasympathomimetics—including pilocarpine, carbachol, cholinesterase inhibitors—including isoflurophate, demecarium bromide, echothiephate iodide; carbonic anhydrase inhibitors—including dichlorophenamide acetazolamide, methazolamide.

Anticataract drugs: such as aldose reductase inhibitors including tolerestat, statol, sorbinil; antioxidants including ascorbic acid, vitamin E; nutritional supplements including glutathione and zinc.

The system of the present invention which includes the device in combination with the active agents is important in treating specific locations of the eye. In that regard, the device 10 may include a layer 26 on one side 28 of the device and/or a portion thereof to provide a means for preventing diffusion of the active agent from a selected area 28 of the device 10, or a side 30, in a direction indicated by arrow 32. In this embodiment, active agent is only released from the device in a direction indicated by arrow 34.

This structure, coupled with the placement of the device 10 within the eye, can be in various positions, as suggested in FIG. 3, enabling the improved delivery of active agents to selected portions of the eye, for example, posterior segments of the eye, i.e., lens, vitreous cavity, and choroid/retina. Thus, the device of the present invention may include specific drugs used to treat diseases of a posterior segment of the eye, for example, including, but not limited to:

Macular degeneration including neovascular inhibitors such as interferon a and amiloride, and nutritional supplements such as zinc.

Cystoid macular edema including nonsteroidal anti-inflammatories such as flurbiprofen, indomethacin, susprofen, volateren (diclofenac).

Retinopathies including cytomegalovirus retinitis such as gangcyclovir and forscanet; herpetic retinitis such as acyclovir.

Probiferative viteroretinopathy including antimetabolites such as 5-fluorouracil, fibrinolytics such as tissue plasminogen activator, streptokinase, urokinase, heparin.

Wound modulating agents such as growth factors including TGFa, TGFb, EGF, FGF, IGF, PDGF, NGF.

Antimetabolites such as 5-fluorouracil, trifluorothymidine, doxorubicin, daunarubicin, bleomycin, cytarabine (ara-c), lathrogens such as b-aminopropionitrile (BAPN), D-penicillamine, interferons.

As a specific example, the device 10 may be placed and the impervious layer 26 applied so that the active agent is released from a side adjacent from the sclera only, thereby decreasing systemic drug absorption through the conjunctival blood vessels.

In combination with any one of the hereinabove-referenced active agents, the subconjunctival ocular insert 10, in accordance with the present invention, may include a combination therewith, a tracer, such as, for example, a fluorescent tracer which provides means for enabling visual indication of the amount of active agent in the device when the device is disposed under the conjunctiva. Suitable fluorescent tracers may include:
Anilino-1-naphthaline sulfonic acid ammonium salt;
Acridine Orange;
Acridine Yellow;
Dichlorofluorescein;
Evans blue;
Fluorescein disodium salt;
Rhodamine B;
Rose bengal; and
Nile red among others.

These tracers may be incorporated into the insert by physical admixture or dissolution into the implant matrix.

Alternative embodiments 60, 62 of the present invention are shown in FIGS. 4 and 5 respectively and include apertures 64, 66 therein which provide means for enabling the devices 60, 62 to be sutured to the conjunctiva and/or sclera to prevent migration after insertion. Preferably the apertures are disposed remote from and isolated from body portions 68, 70 of the devices 60, 62 which include an active agent as hereinabove described in connection with the device 10.

The effectiveness in the device in accordance with the present invention in providing sustained release of an active agent was tested using an elliptically shaped device 60 containing a core reservoir of pilocarpine and alginic acid and surrounded by a hydrophobic ethylene/vinyl acetate copolymer membrane containing di (2-ethylhexyl) phthalate as a diffusion enhancer. The results are reported in the following example:

EXAMPLE

Dutch belted rabbits were denictitated whilst under xylazine/ketamine anesthesia about two weeks prior to dosing.

A device was surgically implanted between the upper palpebral subconjunctival tissue and the adjoining sclera of each rabbit eye.

On days 1, 2, 5 and 7 (i.e., at approximately 24, 48, 120 and 168 hours after the surgical implant), rabbits were euthanized and the devices removed and the eyes rinsed with saline and an aliquot of aqueous humor withdrawn using a tuberculin syringe. Other tissues comprising cornea, upper and lower (separately) bulbar conjunctiva, sclera (upper and lower) and iris/ciliary body (ICB; upper and lower) were removed, weighed and stored frozen at $-20°$ C. until analyzed.

The amounts of pilocarpine in each tissue sample and remaining in the device were quantified using the method of Wood and Robinson for aqueous humor and modified for tissue samples as required.

As shown in FIG. 6 the amount of pilocarpine recovered from the devices after removal from the eye decreased from a mean of about 10.6 mg at 24 hours to about 3.15 mg at 168 hours. This linear decline at a zero-order rate of about 48.8 micrograms/hour demonstrates the drug release rate for the implanted device.

Figure 7:
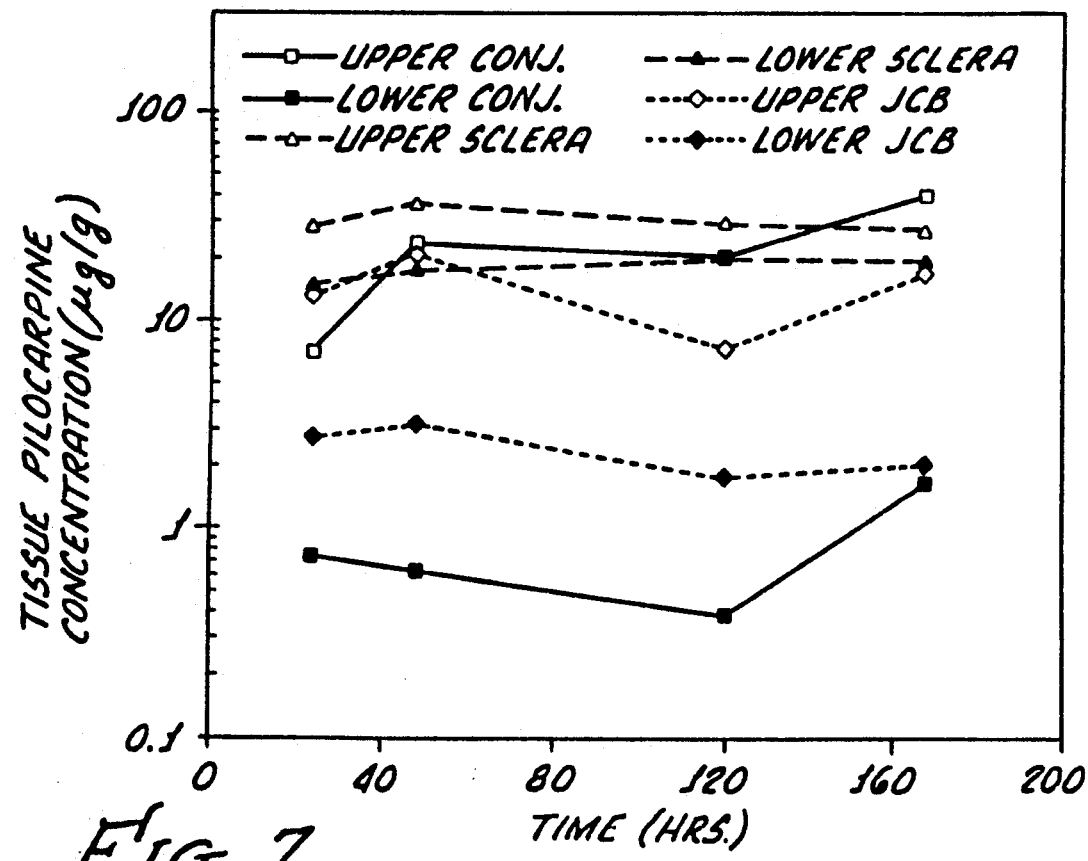
FIG. 7 is a plot of the concentration of pilocarpine released by the device in ocular tissues as a function of time following surgical placement of the device beneath the bulbar conjunctiva of a rabbit.
Figure 8:
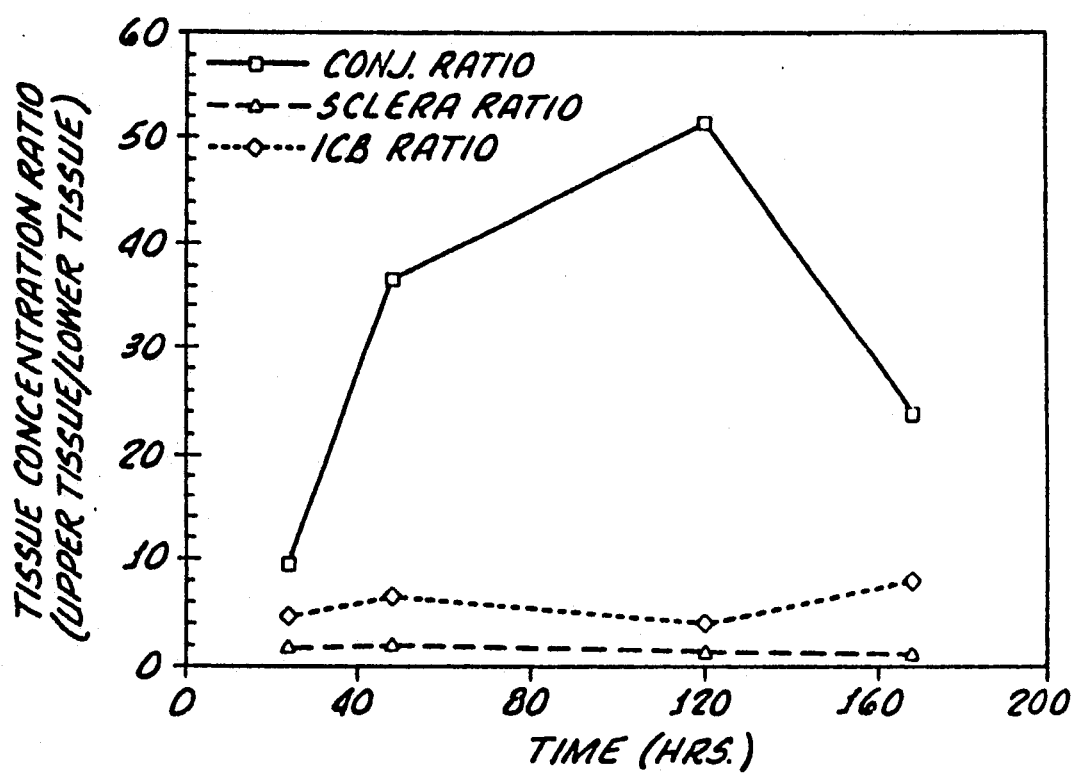
FIG. 8 is a plot of the ratio of upper tissue concentration to lower tissue concentration as a function of time following surgical placement of a device beneath the bulbar conjunctiva of a rabbit.

As shown in FIG. 7, pilocarpine concentrations in the upper conjunctiva ranged from about 7.2 micrograms/gram to about 39.5 micrograms/gram. Concentrations in the lower conjunctiva ranged from about 0.39 microgram/gram to about 1.65 micrograms/gram. There was also a slight upward trend for drug concentration in the lower and upper conjunctivae over the 24- to 168-hour time period. As shown in FIG. 8, the ratio of upper tissue concentration to lower tissue concentration increased from about 9.65 at 24 hours to about 51.5 at 120 hours and then decreased to about 23.9 at 68 hours; the mean upper/lower concentration ratio over time was about 30.5.

As shown in FIG. 7, concentrations in the upper and lower sclera covered a smaller range than in the conjunctivae, and ranged from a minimum of 15.2 micrograms/gram at 24 hours for the lower sclera to as high as 36.6 micrograms/gram at 48 hours for the upper sclera. At all time points, concentrations in the upper sclera were higher than those in the lower sclera. The tissue concentration ratio (see FIG. 8) was essentially constant over time, and the mean upper sclera/lower sclera ratio was about 1.71.

Concentrations in the upper and lower iris ciliary body (ICB) were in a smaller range than tho previously mentioned tissues. Concentrations ranged from about 7.27 to about 20.6 micrograms/gram in the tissue, and from about 1.77 to about 3.15 micrograms/gram in the lower tissue (FIG. 7). In all cases, the amount of drug in the upper tissue was greater than that in the lower. The ratio of upper tissue to lower tissue concentration for ICB was almost constant with respect to time at a mean value of about 5.88 (FIG. 8).

The data presented in FIGS. 6-8 show that preferential drug administration may be accomplished with the device and method of the present invention. Following surgical implantation, drug levels in ocular tissues may be controlled so that the following ranking of preferential drug delivery may be obtained: upper sclera > upper conjunctiva = lower sclera > upper ICB > lower ICB > lower conjunctiva. It should be noted that the distribution around the eye is not uniform since the lower scleral levels greatly exceed those of the lower conjunctiva. It is postulated that this is due to the sclera having a larger intratissue permeability for pilocarpine than the conjunctiva.

In all cases, the mean concentrations in the upper tissues were far greater than those of the lower tissues. The upper to lower ratio was dependent on the tissue studied. The rank order of the ratio was conjunctiva > ICB > sclera.

A method in accordance with the present invention includes the step of disposing a device 10 in a subconjunctival area 40 of an eye and thereafter illuminating the device 10 with an ultraviolet lamp 42 or the like, as shown in FIG. 3, in order to cause a fluorescence of the fluorescent tracer in the device 10 as indicated by the arrows 46 with such fluorescence being visually observed or measured through the use of a detector, not shown.

In this procedure, a short-acting anesthetic such as xylocaine may be injected under the conjunctiva 40 raising a bleb on a paralimibal area for placement of device 10. A Westcott scissors or similar instrument may be used to incise the conjunctiva/tenons to bare sclera and tissue, and thereafter a forceps-type instrument be utilized to thread the device 10 through the conjunctival incision and allow it to rest flat on the sclera. The conjunctival incision may be closed with a suture or allowed to heal without sutures as may be determined by the operating physician.

Alternatively, an insertion device modeled after a commonly used needle syringe may be used to perforate the conjunctiva by pushing on a plunger (not shown) be utilized to inject the device 10 beneath the conjunctival tissue 30.

As hereinabove noted, device 10 may be placed in various locations on the globe 50, including the paralimibal area of the superior or inferior globe, or under a rectus muscle for drug delivery to the muscles.

It should be apparent that the device is readily removed by making an incision in the conjunctiva adjacent to the device and using a forceps to pull the device out when the treatment period is over or when the device has been visually observed to contain insufficient active agent to continue treatment. A repeated insertion of additional devices may be included as determined by the attending physician.

Although there has been hereinabove described a specific arrangement of a system for providing controlled release of an active agent and a subconjunctival ocular insert along with a method for its use, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A subconjunctival ocular implant comprising:
a supply of an active agent
means for supporting said active agent and enabling diffusion of the active agent out of the implant at a selected rate;
means for providing visual indication of the amount of active agent in said ocular implant when said ocular implant is disposed under a conjunctiva of an eye.

2. A subconjunctival ocular implant according to claim 14; wherein said means for supporting said active agent and enabling diffusion of the active agent out of the implant at a selected rate comprises a matrix comprising a polymer, permeable by said active agent, and an impermeable layer, disposed on said matrix, for preventing diffusion of the active agent from a selected area on the means for supporting said active agent.

3. The subconjunctival ocular implant according to claim 2 wherein said impermeable layer is disposed on said matrix for enabling delivery of active agent only to posterior segments of an eye.

4. The subconjunctival ocular implant, according to claim 3, wherein said impermeable layer is disposed on said matrix for enabling delivery of active agent only from a side of the matrix adjacent to a sclera in order to decrease systemic drug adsorption through conjunctival blood vessels.

5. The subconjunctival ocular implant according to claim 1 wherein said means for supporting the active agent comprises a flexible body formed of a polymeric material.

6. The subconjunctival ocular implant according to claim 5 further comprising means for preventing diffusion of the active agent out of the implant from a selected area of the implant.

7. The subconjunctival ocular implant according to claim 6 wherein the selected area comprises a surface on said subconjunctival ocular implant facing said conjunctiva when said subconjunctival ocular implant is disposed under the conjunctiva.

8. The subconjunctival ocular implant according to claim 7 wherein means for providing visual indication comprises a fluorescent tracer.

9. The subconjunctival ocular implant according to claim 8 further comprising means for preventing migration of said implant in the eye after placement of the implant under the eye conjunctiva.

10. The subconjunctival ocular implant according to claim 9 wherein said means for preventing migration of the implant in an eye comprises means for defining an arcuate exterior shape of the implant.

11. The subconjunctival implant according to claim 10 wherein the flexible body shape comprises a crescent.

12. The subconjunctival ocular implant according to claim 9 wherein said means for preventing migration of the implant in an eye comprises means for enabling the implant to be sutured to the sclera.

13. The subconjunctival ocular implant according to claim 9 wherein said means for preventing migration of the implant in an eye comprises means for temporarily bonding the implant to a sclera.

14. The subconjunctival ocular implant according to claim 1 wherein said means for providing visual indication comprises a fluorescent tracer.

15. The subconjunctival ocular implant according to claim 14 wherein the means for supporting said active agent comprises a flexible body formed of a polymeric material permeable to passage of the active agent and having a layer impermeable to the active agent on a side thereof.

* * * * *